(12) United States Patent
Ghamari

(10) Patent No.: US 11,000,255 B2
(45) Date of Patent: May 11, 2021

(54) SYSTEMS AND METHODS FOR GENERATING SIMULATED COMPUTED TOMOGRAPHY (CT) IMAGES

(71) Applicant: BAYER HEALTHCARE LLC, Whippany, NJ (US)

(72) Inventor: Mohammad Sedigh Ghamari, Toronto (CA)

(73) Assignee: BAYER HEALTHCARE LLC, Whippany, NJ (US)

(*) Notice: Subject to any disclaimer, the term of this patent is extended or adjusted under 35 U.S.C. 154(b) by 105 days.

(21) Appl. No.: 16/482,845

(22) PCT Filed: Feb. 22, 2018

(86) PCT No.: PCT/US2018/019282
§ 371 (c)(1),
(2) Date: Aug. 1, 2019

(87) PCT Pub. No.: WO2018/156803
PCT Pub. Date: Aug. 30, 2018

(65) Prior Publication Data
US 2020/0008772 A1 Jan. 9, 2020

Related U.S. Application Data

(60) Provisional application No. 62/463,423, filed on Feb. 24, 2017.

(51) Int. Cl.
*A61B 6/00* (2006.01)
*A61B 6/03* (2006.01)
(Continued)

(52) U.S. Cl.
CPC .............. *A61B 6/583* (2013.01); *A61B 6/032* (2013.01); *A61B 6/12* (2013.01); *G05B 17/02* (2013.01);
(Continued)

(58) Field of Classification Search
CPC .................................................... A61B 6/583
See application file for complete search history.

(56) References Cited

U.S. PATENT DOCUMENTS

| 4,985,906 A | 1/1991 | Arnold |
| 6,907,102 B1 | 6/2005 | Sauer et al. |

(Continued)

FOREIGN PATENT DOCUMENTS

| CN | 102945328 A | 2/2013 |
| JP | 2003280544 A | 10/2003 |

OTHER PUBLICATIONS

Gianaria E. et al., "Real-time Simulation of Radiological Images Using CUDA Technology", 23rd Euromicro International Conference on Parallel, Distributed, and Network-Based Processing, IEEE, 2015, 669-673.
(Continued)

*Primary Examiner* — Hoon K Song
(74) *Attorney, Agent, or Firm* — James R. Stevenson; Bryan Clark

(57) ABSTRACT

Described is a system for generating simulated CT images. The system can include a CT image simulator, a phantom database, and a scanner database. The phantom database can include one or more virtual phantoms while the scanner database can include information about one or more CT scanners, including a subject CT scanner. The CT image simulator can use information about a subject patient, a virtual phantom, and scanner information about the subject CT scanner to generate a simulated CT image that closely simulates what an actual CT image would look like if performed on the subject patient using the subject CT scanner. The simulated CT image can be displayed on a display screen. Also described is a method of generating a simulated CT image and CT image simulator software that can be used to generate a simulated CT image.

21 Claims, 8 Drawing Sheets

(51) Int. Cl.
  *A61B 6/12* (2006.01)
  *G05B 17/02* (2006.01)
  *G06T 11/00* (2006.01)
  *A61B 17/00* (2006.01)

(52) U.S. Cl.
  CPC ........... *G06T 11/005* (2013.01); *A61B 6/5258* (2013.01); *A61B 2017/00716* (2013.01); *G06T 2207/10081* (2013.01)

(56) References Cited

U.S. PATENT DOCUMENTS

| | | | |
|---|---|---|---|
| 8,270,560 B2 * | 9/2012 | Hirokawa | .............. A61B 6/032 378/4 |
| 8,953,861 B2 | 2/2015 | Couch et al. | |
| 8,958,617 B2 | 2/2015 | Couch et al. | |
| 9,192,301 B2 | 11/2015 | Alghamdi et al. | |
| 9,547,893 B2 | 1/2017 | Couch et al. | |
| 9,792,680 B2 | 10/2017 | Couch et al. | |
| 2009/0196393 A1 | 8/2009 | Wang et al. | |
| 2011/0097007 A1 | 4/2011 | Zeng et al. | |
| 2012/0128265 A1 | 5/2012 | Silver et al. | |
| 2013/0315453 A1 | 11/2013 | Cao et al. | |
| 2014/0321608 A1 * | 10/2014 | Ueki | ...................... A61B 6/032 378/18 |
| 2015/0125055 A1 | 5/2015 | Gao et al. | |
| 2016/0367212 A1 | 12/2016 | Tang et al. | |
| 2017/0123074 A1 | 5/2017 | Couch et al. | |
| 2017/0228860 A1 | 8/2017 | Couch et al. | |
| 2017/0243350 A1 | 8/2017 | Couch et al. | |

OTHER PUBLICATIONS

"Radiography training using 3D interactive simulation.", http://www.shaderware.com, Shaderware Ltd., [accessed on or before Feb. 24, 2017].

* cited by examiner

Raw projection for
a single slice

Sinogram

Sinogram

Simulated Slice
Image

SYSTEMS AND METHODS FOR GENERATING SIMULATED COMPUTED TOMOGRAPHY (CT) IMAGES

CROSS REFERENCE TO RELATED APPLICATION(S)

This application is a 371 national phase application of International Application No. PCT/US2018/019282, filed Feb. 22, 2018, and claims the benefit of U.S. Provisional Patent Application Ser. No. 62/463,423, filed Feb. 24, 2017, the entire disclosures of which are hereby incorporated by reference in their entirety.

BACKGROUND

Field of the Invention

This disclosure is related to systems and methods for medical imaging, and, particularly, to systems and methods for generating realistic simulated computed tomography (CT) images based on detailed anthropomorphic computer phantoms.

Description of Related Art

CT imaging is an indispensable diagnostic tool that is widely used in hospitals and medical facilities around the world. The undesirable side effect of CT imaging is exposing the patient to a fairly significant amount of radiation. According to the International Atomic Energy Agency (IAEA), a chest or abdomen CT scan exposes the patient to 5 to 20 mSv as opposed to less than 0.1 mSv in an ordinary chest x-ray. Unfortunately, lowering the exposure in a CT scan has a detrimental effect on the quality of the acquired CT images, which in turn can negatively affect the diagnosis. The rise in the awareness of the harms of exposure to excessive x-ray radiation in CT scans in recent years has resulted in a great focus on the As Low As Reasonably Achievable ("ALARA") principle and has stimulated significant interest in ways to optimize CT imaging. Currently estimating exposure and monitoring radiation dose is available and widely used. One of the most prominent such uses is through the Radimetrics™ Enterprise Platform available from Bayer HealthCare LLC. In contrast, so far there has been inadequate focus on a comprehensive and reliable solution to preemptively ensure that the quality of the image will be sufficient for diagnosis purposes without also exposing the patient to excessive and unnecessary radiation.

SUMMARY

An object of certain embodiments of this disclosure is to provide a way to simulate the results of a CT scan performed by a subject CT scanner on a subject patient. As will become apparent in the following paragraphs, the embodiments described herein relate to systems and methods for generating simulated CT images. The simulated CT images take into account the actual physical characteristics of the subject patient and the actual information used by the subject CT scanner to capture image data and transform it into reconstructed images. The result is a simulated image that closely resembles the image that would be generated if the CT scan was performed by the subject CT scanner on the subject patient.

Various aspects of the present disclosure may be further characterized by one or more of the following clauses:

Clause 1: A method of generating simulated CT images of a subject patient, comprising: receiving patient information about the subject patient, wherein the patient information comprises information about one or more physical properties of the subject patient; selecting, from a phantom database, a virtual phantom, wherein the selection is based on a comparison of the patient information with characteristics of the virtual phantom; receiving, at a CT image simulator, the virtual phantom; receiving, at the CT imaging simulator, scanner information about a subject CT scanner, wherein the scanner information comprises information about an image reconstruction technique employed by the subject CT scanner; performing, by the CT imaging simulator, an image simulation process, wherein the image simulation process comprises generating a simulated CT image using the virtual phantom and the scanner information; and providing the simulated CT image on a display screen in a visually perceptible form.

Clause 2: The method of clause 1, further comprising: deforming the virtual phantom, wherein deforming the virtual phantom comprises one or more of adjusting the shape of organs in the virtual phantom, adjusting tissue densities in the virtual phantom using the patient information, and incorporating an implant into the virtual phantom.

Clause 3: The method of clause 2, wherein deforming the virtual phantom comprises adjusting the tissue densities using the patient information, wherein the patient information comprises bone density information of the subject patient.

Clause 4: The method of clause 2 or 3, wherein deforming the virtual phantom comprises incorporating the implant into the virtual phantom.

Clause 5: The method of any of clauses 1-4, wherein at least a portion of the scanner information is received from a scanner database in communication with the CT imaging simulator.

Clause 6: The method of any of clauses 1-5, wherein at least a portion of the scanner information is received from a user interface associated with the CT imaging simulator, wherein the at least a portion of the scanner information has been manually entered by a user into the user interface.

Clause 7: The method of any of clauses 1-6, wherein the CT image simulator is in communication with the subject CT scanner and at least a portion of the scanner information is received from the subject CT scanner.

Clause 8: The method of any of clauses 1-7, further comprising: receiving, at the CT image simulator, an identity of the subject CT scanner; and querying, by the CT image simulator, a scanner database for scanner information about the subject CT scanner, wherein the query is based on the identity of the subject CT scanner.

Clause 9: The method of any of clauses 1-8, wherein selecting the virtual phantom is performed by the CT imaging simulator based on a comparison of the patient information with characteristics of the virtual phantom done by the CT imaging simulator.

Clause 10: The method of any of clauses 1-9, wherein the one or more physical properties of the subject patient include at least one of age, height, body size, sex, weight, and body mass index.

Clause 11: The method of any of clauses 1-10, wherein the image simulation process comprises generating projection images.

Clause 12: The method of any of clauses 1-12, wherein the image simulation process comprises performing an attenuation to linear attenuation conversion according to the following equation:

$$-\ln(A_\delta) = -\ln(e^{-\Sigma_{Organs} \mu_{organ} d_{organ}} + \delta).$$

Clause 13: The method of any of clauses 1-13, wherein the image simulation process comprises performing a reconstruction in order to generate a simulated slice image.

Clause 14: A system, comprising: a CT image simulator, comprising a user interface, a display screen, a processor, and a non-transitory storage medium comprising programming instructions; a phantom database in communication with the CT image simulator, wherein the phantom database comprises one or more virtual phantoms; and a scanner database in communication with the CT image simulator, wherein the scanner database comprises information about one or more CT scanners, including a subject CT scanner; wherein the programming instructions, if executed, enable the processor to: receive patient information about a subject patient, wherein the patient information comprises information about one or more physical properties of the subject patient; receive from the phantom database a virtual phantom, wherein the virtual phantom has been selected based on a comparison of the patient information with characteristics of the virtual phantom; receive scanner information about the subject CT scanner, wherein the scanner information comprises information about an image reconstruction technique employed by the subject CT scanner; perform an image simulation process, wherein the image simulation process comprises generating a simulated CT image using the virtual phantom and the scanner information; and provide the simulated CT image on the display screen in a visually perceptible form.

Clause 15: The system of clause 14, wherein the programming instructions, if executed, further enable the processor to receive at least a portion of the scanner information from the scanner database.

Clause 16: The system of clause 14 or 15, wherein the programming instructions, if executed, further enable the processor to query the scanner database for scanner information about the subject scanner, wherein the query is based on an identity of the subject CT scanner.

Clause 17: The system of any of clauses 14-16, wherein the programming instructions, if executed, further enable the processor to deform the virtual phantom, wherein deforming the virtual phantom comprises one or more of adjusting the shape of organs in the virtual phantom, adjusting tissue densities in the virtual phantom using the patient information, and incorporating an implant into the virtual phantom.

Clause 18: CT image simulator software stored on a non-transitory storage medium to generate a simulated CT image of a subject patient, the software comprising programming instructions that, if executed, enable a processor to: receive patient information about the subject patient, wherein the patient information comprises information about one or more physical properties of the subject patient; receive a virtual phantom, wherein the virtual phantom has been selected based on a comparison of the patient information with characteristics of the virtual phantom; receive scanner information about a subject CT scanner, wherein the scanner information comprises information about an image reconstruction technique employed by the subject CT scanner; perform an image simulation process, wherein the image simulation process comprises generating a simulated CT image using the virtual phantom and the scanner information; and provide the simulated CT image in a visually perceptible form.

Clause 19: The CT image simulator software of clause 18, wherein the programming instructions, if executed, further enable the processor to receive at least a portion of the scanner information from a scanner database.

Clause 20: The CT image simulator software of clause 19, wherein the programming instructions, if executed, further enable the processor to query the scanner database for scanner information about the subject CT scanner, wherein the query is based on an identity of the subject CT scanner.

Clause 21: The CT image simulator software of any of clauses 18-20, wherein the programming instructions, if executed, further enable the processor to deform the virtual phantom, wherein deforming the virtual phantom comprises one or more of adjusting the shape of organs in the virtual phantom, adjusting tissue densities in the virtual phantom using the patient information, and incorporating an implant into the virtual phantom.

Clause 22: The system of clause 14, wherein the programming instructions, if executed, enable the processor to perform the method of any of clauses 1-13.

Clause 23: The CT image simulator software of clause 18, wherein the programming instructions, if executed, enable the processor to perform the method of any of clauses 1-13.

DETAILED DESCRIPTION

Figure 1:
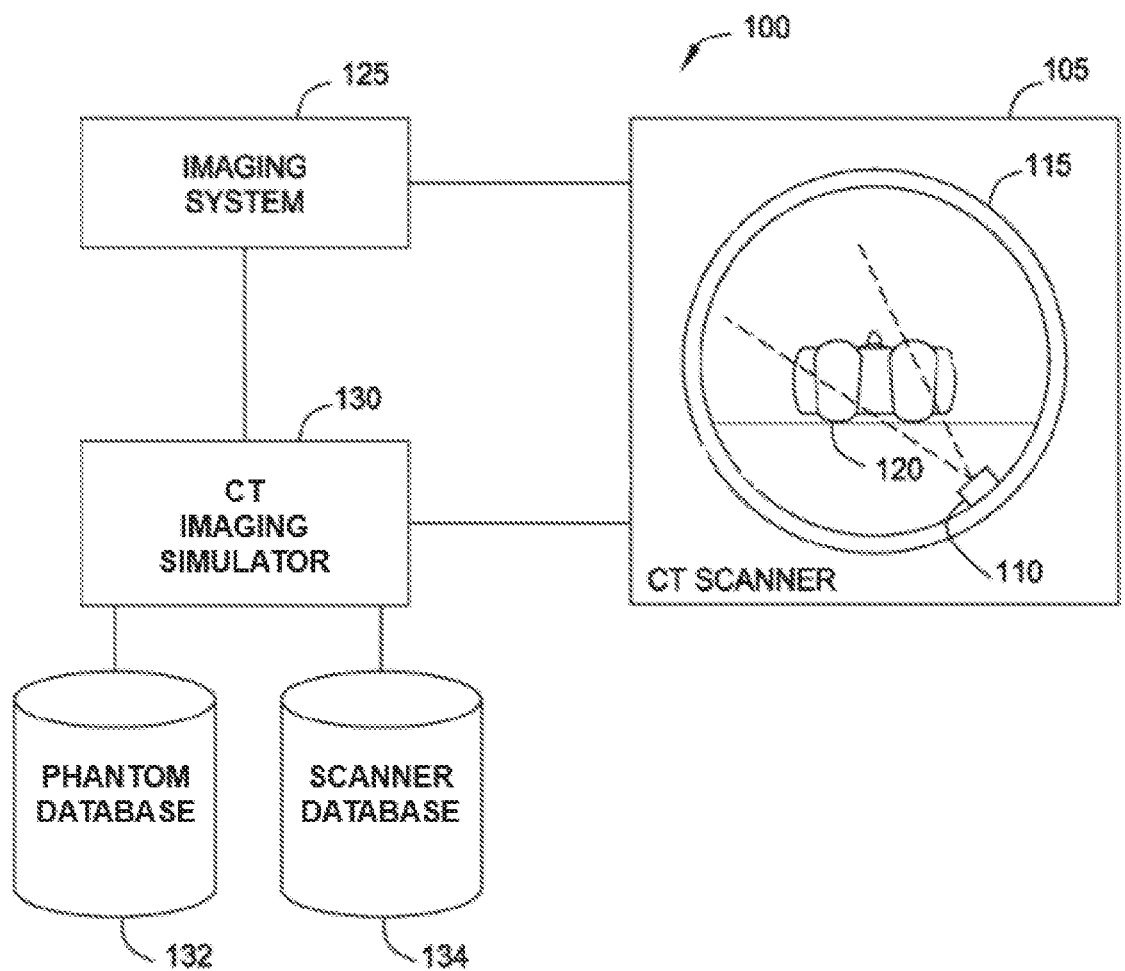
FIG. 1 illustrates a CT scanning environment and related computing systems according to one non-limiting embodiment.

For purposes of the description hereinafter, spatial orientation terms shall relate to the embodiment as it is oriented in the drawing figures. However, it is to be understood that the various embodiments of this disclosure may assume alternative variations and step sequences, except where expressly specified to the contrary. It is also to be understood that the specific devices and processes illustrated in the attached drawings, and described in the following specification, are simply exemplary. Hence, specific dimensions and other physical characteristics related to the embodiments disclosed herein are not to be considered as limiting.

As used in the specification, the singular form of "a", "an", and "the" include plural referents unless the context clearly dictates otherwise.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

All documents, such as but not limited to issued patents and patent applications, referred to herein, and unless otherwise indicated, are to be considered to be "incorporated by reference" in their entirety.

Embodiments of the disclosure are generally directed to methods and systems for simulating images that would be generated during computerized tomography (CT) scans. More specifically, embodiments of the disclosure provide approaches for generating a simulated image that accurately represents the image that would be generated if a subject patient were actually subjected to a CT scan using a subject scanner. As described in detail below, the CT imaging simulator system provides a useful tool for medical personnel to prospectively assess how a particular CT image may look as well as to retroactively assess how a particular CT imaging procedure could have been improved. Consideration of CT image simulations in ordering diagnostic imaging tests may lead to a more informed decision-making process and ultimately benefit patient safety and care.

FIG. 1 illustrates an example of a CT scanning environment 100 and related computing systems configured to provide a simulated CT image, according to one embodiment of the invention. As shown, the CT scanning environment 100 includes a CT scanner 105, an associated imaging system 125, and a CT imaging simulator 130. Additionally, the CT imaging simulator 130 can include a phantom database 132 and a scanner database 134.

As is known, the CT scanner 105 provides a device used to bombard a subject 120 with X-rays from an X-ray source 110. The X-rays emitted from X-ray source 110 pass through tissues, organs, and structures of the subject 120 at different rates (some of which is absorbed by such tissues organs and structures) depending on the density and type of matter which the X-rays pass through. Sensors disposed with a ring 115 detect the amount of radiation that passes through the subject 120. The resulting sensor information is passed to imaging system 125. The imaging system 125 provides a computing device configured to receive, store, and generate images from the sensor data obtained from the CT scanner 105.

CT scanning images (often referred to as "slices") are typically made relative to an axial or transverse plane, perpendicular to the long axis of the body. However, CT scanner 105 may allow the imaging data to be reformatted in various planes or as volumetric (3D) representations of structures. Once a CT scan is performed, the imaging data generated by CT scanner 105 may be stored allowing the resulting scan images to be reviewed or evaluated in other ways. In one embodiment, imaging data may be formatted using the well-known DICOM standard and stored in a PACS repository.

In one non-limiting embodiment, the CT imaging simulator 130 provides a computing system and software applications configured to generate a simulated image that corresponds to an image that would be generated by the imaging system 125 if a given patient were to be subject to a CT scan by the CT scanner 105. This simulation may be made in a predictive sense (i.e., before performing a scan) but may be made after the scan as well. The CT imaging simulator 130 can include at least a processor and software instructions stored in non-transitory machine-readable media that, when executed, enable the processor to perform the operations discussed herein. The CT imaging simulator 130 may also include one or more hardware components, such as a user interface for entering commands, such as a keyboard, mouse, touchscreen, or wired or wireless device (e.g., a smartphone, laptop, remote control, or PDA) in communication with CT imaging simulator 130, as well as a display for displaying images.

As will be apparent from reading the disclosure below, while the phantom database 132 and scanner database 134 are shown as being part of the CT imaging simulator 130, each of these databases can be located remotely from the CT imaging simulator 130 and even from the CT scanning environment 100. For example, one or more of these databases may be remotely located and accessible by CT imaging simulator 130 through a network connection, such as an Intranet, LAN, WAN, or an Internet connection. By way of another example, one or more of these databases may be a cloud-based database accessible by the CT imaging simulator 130 through the Internet. In some non-limiting embodiments, the scanner database 134 may not be necessary as the CT imaging simulator 130 may be capable of receiving the necessary information from the CT scanner 105 itself.

Figure 2:
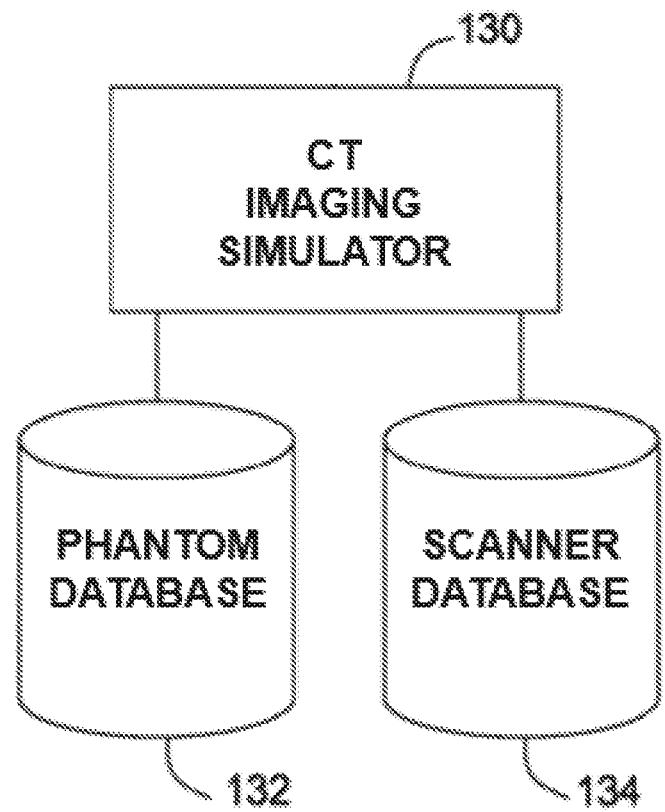
FIG. 2 illustrates a CT imaging simulator and related components according to one non-limiting embodiment.

In some non-limiting embodiments, as depicted in FIG. 2, the CT imaging simulator 130 may be a standalone system that is not associated with the remaining components of the CT scanning environment 100. In this embodiment, the CT imaging simulator 130 may have phantom database 132 and scanner database 134 associated therewith or, as described above, these databases may be located remotely from CT imaging simulator 130 and accessible through a network, which may include the Internet.

Figure 3:
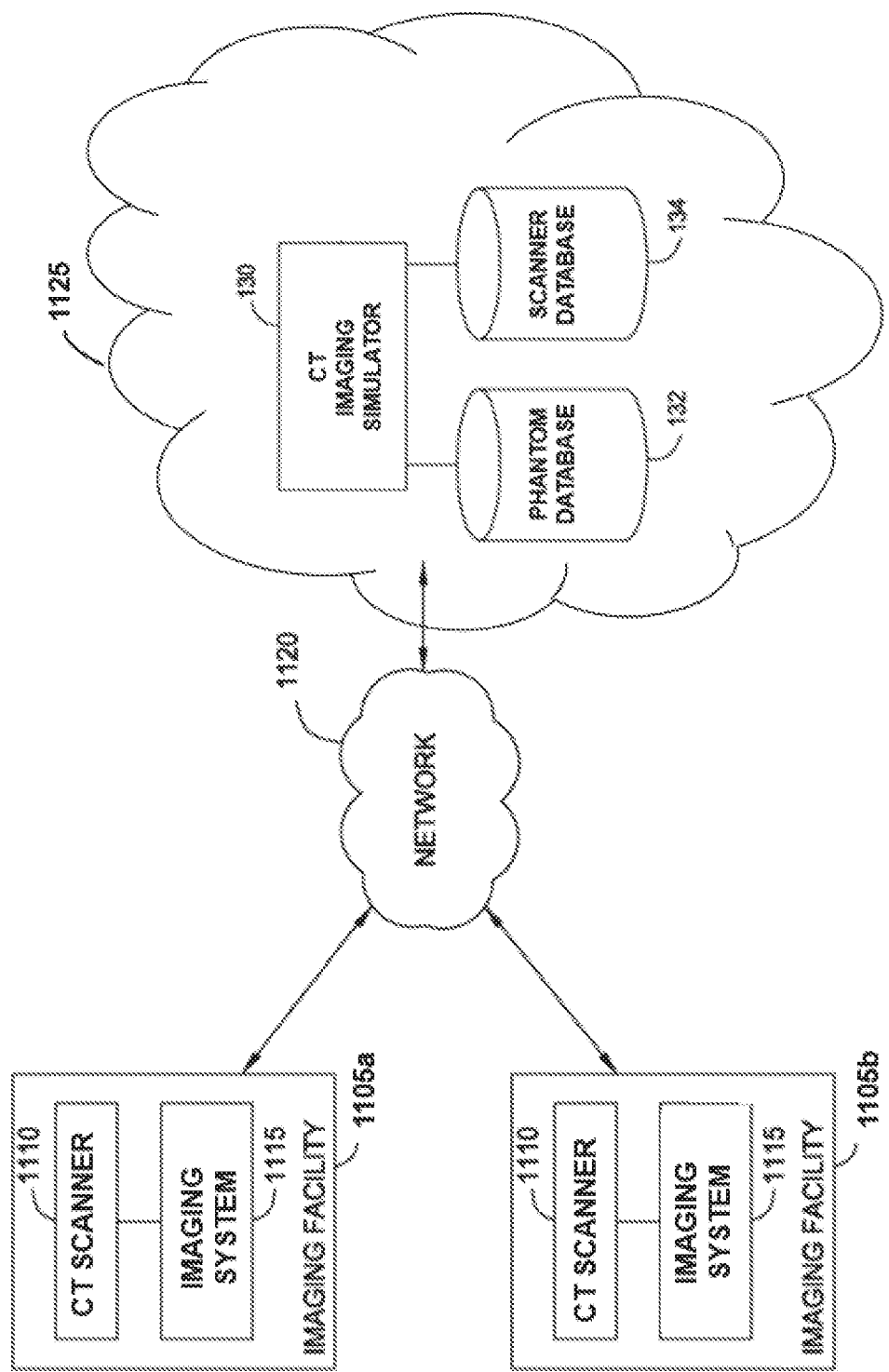
FIG. 3 illustrates a networked CT scanning environment and related computing systems according to one non-limiting embodiment.

In yet another embodiment, depicted in FIG. 3, CT imaging simulator 130 can be associated with a plurality of CT scanners 1110 and/or a plurality of imaging systems 1115, such as through a network, such as a local area network, a cloud based network, a wide area network, an Internet, an Intranet, or another suitable network. As shown, a cloud based provider 1125 hosting a CT imaging simulator 130 can communicate over network 1120 with imaging facilities 1105a-b. At each imaging facility 1105, a CT scanner 1110, including an associated imaging system 1115, are used to provide imaging services for patients.

Phantom database 132 includes imaging phantoms. Imaging phantoms are well known in the art and can be generally described as a model of the human body, or a portion thereof, that can be used in ionizing radiation studies in place of an actual human being. Over time, these phantoms have become increasingly accurate with respect to the internal structure of the human body. Phantoms can be physical phantoms, which usually take the form of a specially designed object, such as a cylinder or series of cylinders holding various liquids or semi-liquids that have the approximate density of the human body and the organs thereof. Exemplary physical phantoms are those discussed in U.S. Pat. No. 4,985,906, which is incorporated herein by reference. Phantoms can also be mathematical models of the human body, also referred to herein as virtual phantoms. For purposes of this disclosure, mathematical, or virtual, phantoms are stored in phantom database 132.

Figure 4:
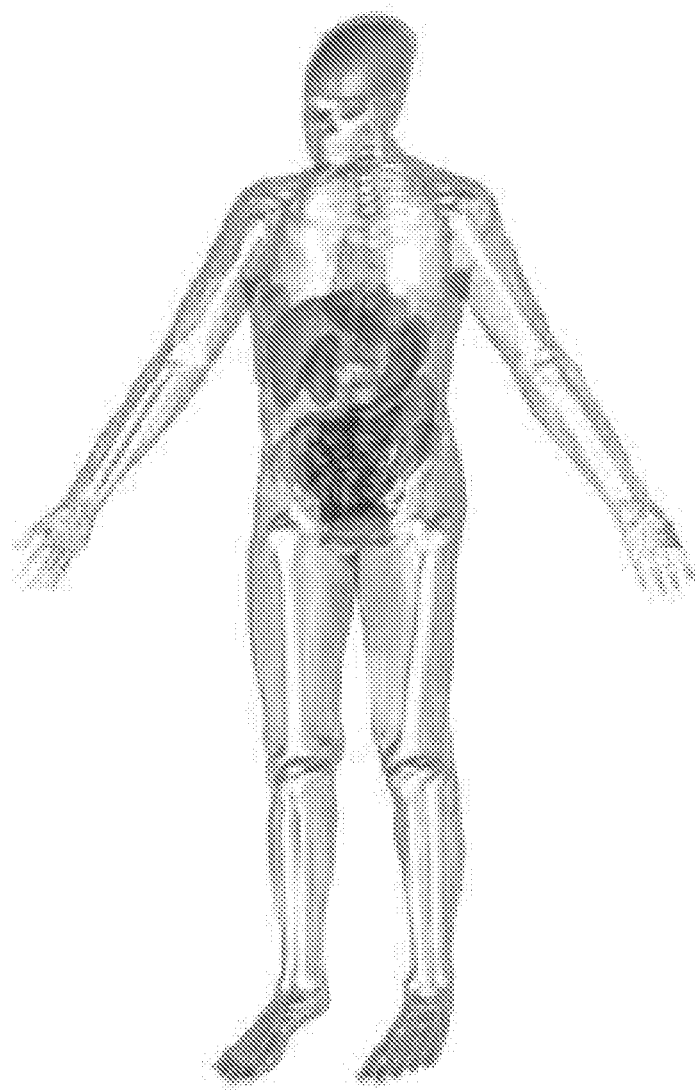
FIG. 4 illustrates a representation of a mesh virtual phantom with organs according to one non-limiting embodiment.

Virtual phantoms can provide accepted mathematical models of portions of human tissue, organs, structures, etc. For example, virtual phantoms may provide a set of non-uniform rational basis spline (NURBS) used to create a three-dimensional model of a human body (or portion thereof). Alternatively, the virtual phantoms may be represented using constructive solid geometry (CSG) or other mathematical representation. Examples of suitable virtual phantoms include volumetric (voxel) or surface based (mesh or NURBS) phantoms. An example of a virtual phantom that may be useful in the present disclosure is provided in FIG. 4. The phantom of FIG. 4 includes individual organs and potentially finer details such as the circulatory system, pacemaker, metallic implants, tumors, etc. of the patient. Such phantoms can be created by loading organs into the computer memory individually as non-intersecting closed volumes. The organs are organized in a hierarchy based on which organs are enclosed within which (e.g., brain is contained in skull). The hierarchy of organs on the basis of encompassment is necessary for determining the traversed lengths by each ray within organs. Next, tissue material and densities (as described by ICRP or NIST tables) are assigned to organ volumes, e.g., bone material to bones, soft tissue to muscles, and so on. This may be done automatically based on the organ names but a user would have the option to modify the automatic assignment of tissue materials and densities to suit his or her needs.

Phantom database 132 can be pre-populated with a set of available imaging phantoms that have been previously created. Additional phantoms can be added to phantom database 132 when they are created. The phantoms in phantom database 132 can also be periodically updated or adjusted by modifying the particular characteristics of the phantoms based on, for example, additional information that is learned about the accuracy or performance of the phantom. Virtual phantoms useful in the present disclosure can also be constructed from CT images of the patient. In some embodiments, the CT images themselves, particularly if they are not cropped, can be used as phantoms for image simulation as the image simulation process described herein can be performed without requiring organ segmentation.

CT imaging simulator 130 can communicate with phantom database 132 in order to receive phantoms from phantom database 132, according to the process described below. The communication between CT imaging simulator 130 and phantom database 132 can be by any type of communication known in the art, including through a wired connection or a wireless connection. By way of example only, CT imaging simulator 130 can communicate with phantom database 132 through a wired or wireless LAN, VPN, or WAN connection. Phantom database 132 may also be a cloud-based database that can be accessible over the Internet. This embodiment provides the added benefit that phantom database 132 can be shared between multiple CT imaging simulators 130 that may be remote from one another, such as in different imaging facilities or even in different parts of the world. Phantom database 132 can store the phantoms in any suitable data structure. For example, phantom database 132 can be a relational database using Structured Query Language (SQL) for querying and maintaining phantom database 132. Phantom database 132 should be arranged such that CT imaging simulator 130 can query phantom database 132 and locate phantoms that have characteristics that compare favorably (e.g., closely) with the physical properties and characteristics of the subject patient.

Scanner database 134 includes information about one or more CT scanners. The CT scanners for which information can be contained in scanner database 134 can include CT scanner 105 that is part of the scanning environment 100. It can also include each of CT scanners 1110 that are part of one or more imaging facilities 1105a-b. Still further, scanner database 134 can include information about any number of commercially available CT scanners. For purposes of this disclosure, "scanner information" for a certain CT scanner may also include information relating to imaging system(s) 125, 1115 that are associated with the subject CT scanner, as will be apparent from the discussion herein. As will be appreciated from reading this disclosure, the more CT scanners for which information is stored in scanner database 134, the more powerful and useful CT imaging simulator 130 can become. However, the information in scanner database 134 need not be limited to information concerning commercially available CT scanners, and the information can also relate to theoretical CT scanners. Such information would be useful if CT imaging simulator 130 is used for educational or training purposes where no actual patient is scheduled for a CT procedure.

As is known in the art, a CT scanner includes a detector array, including a series of detector elements, that produces similar signals through various positions as a gantry is displaced around a patient. Various algorithms and operating parameters control how the CT scanner performs each operation. While there is a general set of principles that inform what these algorithms and operating parameters should be, each commercial CT scanner may have slight variations in these algorithms and operating parameters.

The scanner information that can be stored in scanner database 134 can include information about these, and other, parameters and operational details concerning how the subject scanner performs a scan operation to generate raw data (including the scan parameters such as timing and tube voltage), how the scanner collects the raw data (including how the detector array functions), and how the scanner generates images from the raw data (including how the raw data is reconstructed into an image). For example, the scanner database 134 can include information about the algorithms used by the scanner to reconstruct images from the raw data generated by the scan operation. The information stored about each scanner in scanner database 134 should be sufficiently complete and detailed to enable CT imaging simulator 130 to perform an image simulation using the same, or similar, image reconstruction techniques as are used by the scanner so as to accurately simulate an image that would be generated by the scanner when using those same techniques. Examples of reconstruction techniques that may be used for image reconstruction include those discussed in United States Patent Application Publication No. 2009/0196393, United States Patent Application Publication No. 2012/0128265, United States Patent Application Publication No. 2005/0259780, United States Patent Application Publication No. 2011/0097007, United States Patent Application Publication No. 2015/0125055, and U.S. Pat. No. 6,907,102, each of which is incorporated herein by reference.

The accuracy of the simulated image generated by CT imaging simulator 130 for a particular subject scanner will depend on the accuracy and amount of information of the subject scanner contained in scanner database 134. For example, while CT imaging simulator 130 can use baseline or default image reconstruction information that is generally known in the art to perform the simulation, if the subject CT scanner does not follow the baseline image reconstruction technique, the simulated image may not accurately depict how an actual image of the subject CT scanner would appear. On the other hand, if scanner database 134 contains all or most of the details regarding the image reconstruction technique performed by the subject scanner, the CT imaging simulator 130 can access this information and apply it during the simulation to generate a simulated image that would closely match an image that the subject CT scanner would generate after performing the scan.

One non-limiting example of scanner information that could be stored in scanner database 134 is the x-ray beam specifications for initial (i.e., unattenuated) ray spectra, such as the details of flat and shaped filters and the x-ray source. Another non-limiting example is the specification of the detector array of the scanner as well as the detector efficiency and response threshold. Yet another non-limiting example, also mentioned above, is the reconstruction algorithm(s) of the scanner for identical image reconstruction from simulated sinograms. Of these examples, the reconstruction algorithms could be considered the most significant since, in some scanners, the image reconstruction is accomplished based on iterative approaches while other scanners employ filtered back projection algorithms. Certain artifacts in reconstructed CT images generally depend on the details of the algorithms used for reconstructing the images, and accurately reproducing these artifacts in the simulated image depends on knowing the details of these algorithms. By way of example only, while streakiness of the noise in axial CT images is rather universal, where and how the noise streaks appear may to some degree depend on the specifics of image reconstruction. This is particularly the case when one is dealing with starburst artifacts, which may be regarded as very dense noise streaks. However, the intended purpose of using scanner information in the context of noise extends beyond determining the streakiness of the noise and includes, for example, any non-random artifacts associated with the noise streaks, such as tendency to aggregate in a specific way, which would not be entirely stochastic.

Information can be stored in scanner database 134 in any known data structure. For example, scanner database 134 can be a relational database using Structured Query Language (SQL) for querying and maintaining scanner database 134. By way of example only, scanner database 134 can be structured such that each row in scanner database 134 can represent a different CT scanner identified by manufacturer, model, manufacture date, and/or serial number while each column can represent a type of scanner information particular to that scanner. Each CT scanner could also be identified using custom names assigned by the imaging facility (e.g., "CT Room 1 Scanner," "CT Room 2 Scanner," etc.). As with phantom database 132, scanner database 134 can be cloud based such that it is accessible over, for example, the Internet.

Figure 5:
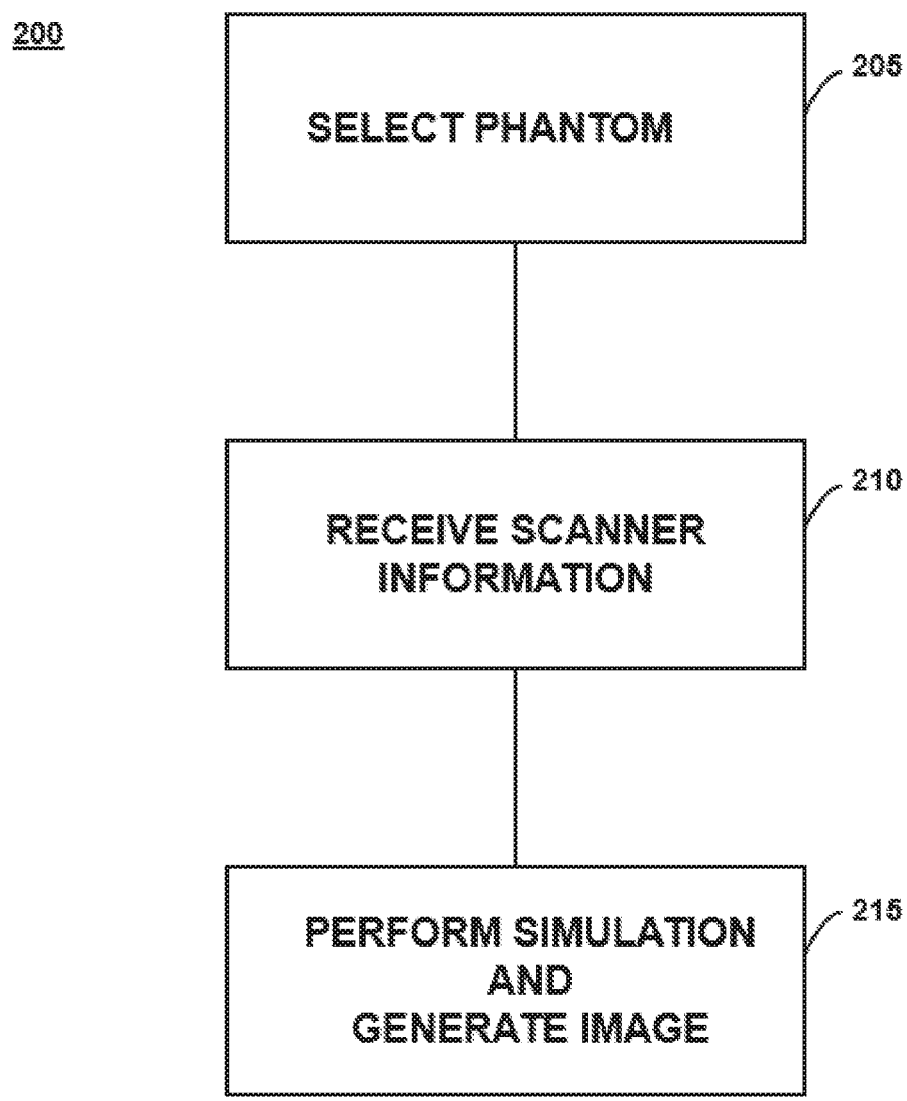
FIG. 5 illustrates a flow diagram of a method of generating a simulated CT image according to one non-limiting embodiment.

FIG. 5 illustrates a method 200 for operating CT imaging simulator 130 to generate a suitable simulated CT image for a subject patient according to one embodiment. As shown, the method 200 begins at step 205, where the CT imaging simulator 130 selects a virtual phantom from the phantom database 132. At step 210, the CT imaging simulator 130 receives scanner information of a subject CT scanner, which may be the CT scanner 105 of the CT imaging environment 100. Some or all of this scanner information may be received from the scanner database 134, while some or all of the information may also be received directly from CT scanner 105 or through a user input into the user interface of CT imaging simulator 130. At step 215, the CT imaging simulator 130 performs an image simulation and generates a simulated image which can be displayed on a display screen. Each of these steps will be further explained below. Steps 205 and 210 can be performed in any order, and can even be performed simultaneously, provided they are performed before step 215.

At step 205, the CT imaging simulator 130 selects, from the phantom database 132, a virtual phantom to be used for the image simulation. The process of selecting the appropriate phantom generally begins by receiving, at the CT imaging simulator 130, characteristics of the subject patient, such as physical properties of the subject patient. Examples of such characteristics include the patient's age, height, body size, sex, weight, body mass index (BMI), etc. This information can be received from, for example, the Hospital Information System (HIS), the Radiology Information System (RIS), or another information source within or available to the imaging facility. This information may also be entered by a user directly into CT imaging simulator 130 through the user interface thereof. Once this information is received, CT imaging simulator 130 can query phantom database 132 to find a phantom that has characteristics that closely align with the characteristics of the subject patient. Alternatively, a user can select a particular phantom from phantom database 132 to use for the simulation. In either case, the selection process may additionally consider information about prior imaging procedures of the patient, such as whether a particular phantom was used with this patient in the past.

As part of the phantom selection step 205, the phantom selected from phantom database 132 may be deformed to better align the characteristics of the phantom with the subject patient, including BMI, height, gender, and other anatomical metrics. This modification process may be initiated and controlled by the operator using software associated with the CT imaging simulator 130 or, alternatively, it may be automatically performed by the CT imaging simulator 130. In one non-limiting embodiment, the phantom can be modified to better align the tissue and/or bone density representations of the phantom with known tissue and/or bone density information of the subject patient. For example, a patient diagnosed with osteoporosis would have a lower bone density. The tissue material and density affect the attenuation of the x-ray beam as it passes through the phantom organs during the simulation. In another non-limiting embodiment, other details such as a pacemaker and metallic or other implants can also be incorporated into the phantom. If the phantom has a circulatory system, the user can specify at this point if a contrast material is present and set the related parameters.

In one embodiment, the CT imaging simulator 130 may be configured to deform a virtual phantom to better model a particular patient using the techniques described in U.S. Pat. Nos. 8,958,617 and 9,547,893 and U.S. Patent Application Publication Nos. 2017/0228860 and 2017/0243350, the contents of which are incorporated herein by reference. Suitable deformations include adjusting the shape of the organs and adjusting the tissue densities using information about the subject patient, such as existing images of the patient.

At step 210, CT imaging simulator 130 receives scanner information related to a subject CT scanner. The subject CT scanner is the CT scanner that is scheduled to be used (or that was used) to perform the CT scan on the subject patient. However, the subject CT scanner may instead be a different scanner, which may be the case if the CT imaging simulator 130 is used for educational or training purposes where no patient is scheduled for a CT procedure.

CT imaging simulator 130 can receive scanner information from a variety of sources. A primary source of this information may be scanner database 134 which, as discussed above, stores information about one or more CT scanners. Once CT imaging simulator 130 is aware of the identity (e.g., the manufacturer, model, manufacture date, serial number, etc.) of the subject CT scanner, CT imaging simulator 130 can query scanner database 134 for information about this scanner and retrieve any information about the subject CT scanner from scanner database 134. CT imaging simulator 130 can learn the identity of the subject CT scanner from, for example, a user entering that information into CT imaging simulator 130 or selecting the subject CT scanner from a pre-populated list on CT imaging simulator 130. Alternatively, information received from HIS, RIS, or another information source may provide the identity of the subject CT scanner to CT imaging simulator 130. By way of another example, if the subject CT scanner and CT imaging simulator 130 are in communication, CT imaging simulator 130 can query the subject CT scanner for this information.

In addition to receiving scanner information from scanner database 134, scanner information can be provided to CT imaging simulator 130 by a user through the user interface of CT imaging simulator 130. Scanner information can also be sent from the subject CT scanner to CT imaging simulator 130. These methods of receiving scanner information are particularly suitable for scanner information that can vary from scan to scan and patient to patient, such as the tube voltage or kVP. This communication can be directly from the scanner to the CT imaging simulator through a wired (e.g., LAN, WAN) or wireless (e.g., Wi-Fi, Bluetooth, ZigBee) connection. The communication could also be indirect, such as through one or more intermediary systems or networks, for example an injector system. In another non-limiting embodiment, CT imaging simulator 130 can receive the scanner information by retrieving it from a local storage device associated with CT imaging simulator 130, such as a hard drive, or from a removable storage device, such as a USB flash drive, CD, or DVD.

As mentioned above, scanner information is preferably tied to, and specific for, the subject CT scanner, though scanner information used by CT imaging simulator 130 can also be partially or entirely derived from generic or default information, such as default image reconstruction information, that is generally known in the art, if such information is not available for the subject CT scanner. For example, if CT imaging simulator 130 receives some, but not all, of the scanner information necessary to follow the image reconstruction technique performed by the subject CT scanner, CT imaging simulator 130 can fill in any gaps with generic or default information that may be stored in scanner database 134 or locally on CT imaging simulator 130. As another alternative, CT imaging simulator 130 may fill in any gaps in the scanner information related to the subject CT scanner using scanner information from a similar scanner for which the information is known. For example, if the subject CT scanner is a new model from a certain manufacturer and scanner database 134 does not contain information on that particular model, CT imaging simulator 130 may instead retrieve information about a different scanner from that same manufacturer, such as the newest model from that manufacturer contained in scanner database 134.

At step 215, once the scanner information is received and the phantom is selected, CT imaging simulator 130 performs an image simulation process in which a series of projections are performed on the phantom using the scanner information so as to generate a simulated image.

The image simulation can be performed using a simulation algorithm. The simulation algorithm can be in the form of software instructions stored in non-transitory machine-readable media associated with the CT imaging simulator 130. These instructions can be executed by a processor associated with the CT imaging simulator 130.

Figure 6:
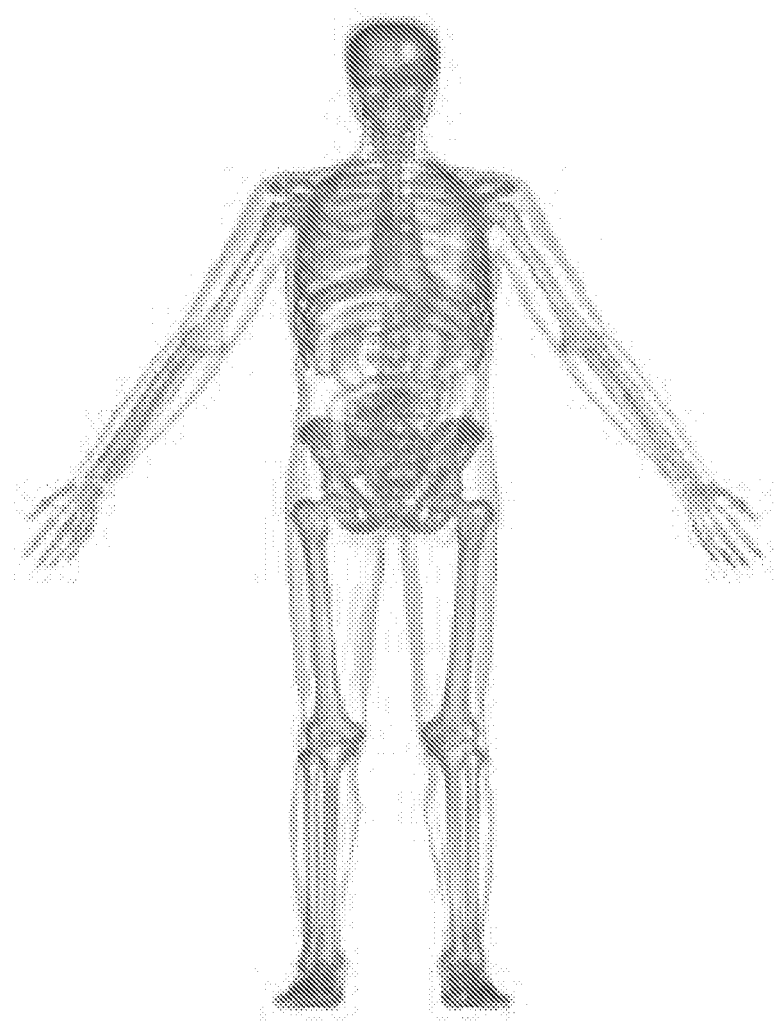
FIG. 6 illustrates a depiction of a single planar projection of a full phantom instance performed as part of the imaging simulation process according to one non-limiting embodiment.

The image simulation process can begin by generating raw data in the form of projection images. Projections are known in the art and are similar to ordinary radiograph images that are projected onto various planes around the phantom. With reference to FIG. 6, shown is a depiction of a single planar projection of a full phantom instance. Depending on what imaging protocol is intended, a full phantom instance may not be needed and a partial projection of a portion of the phantom, such as a projection of only the head or torso, may suffice. The specifics of these raw images, such as the dimensions and pixel spacing, among others, largely depend on the scan range that the user provided and the scanner information of the subject CT scanner received in step 210.

The projections can be done in a variety of ways, as would be appreciated by one of skill in the art. The selection of the projection method may depend on, for example, whether a two-dimensional or three-dimensional reconstruction is intended. If a three-dimensional reconstruction is intended, the projection can be a wide-angle cone helical projection together with known reconstruction methods, such as ones based on the Feldkamp-Davis-Kress (FDK) algorithm or Katsevich's reconstruction algorithm, that can be used to simulate wide-angle cone helical scans. If a two-dimensional reconstruction is intended, projections onto planes (also referred to as slice projections) can be used.

Algorithmically, a projection, whether wide-angle cone or planar projection, can involve determining the intersections of rays with boundaries of the organs, when using surface-based phantoms, or determining directly the length traversed in a single medium for voxel phantoms. The tissue composition of organs is then incorporated into determining the total attenuation for the simulated ray. The attenuation factor can be expressed according to the formula:

$$A = e^{-\Sigma_{Organs} \mu_{organ} d_{organ}}$$

where $\mu_{Organ}$ is the linear attenuation coefficient of the organ (depends on energy/kVp) and $d_{Organ}$ is the length traversed in the organ by the ray.

After the projection step is complete, the two-dimensional projection images may be reorganized. This reorganization process is intended to generally mirror the way CT scanners reorganize the raw acquired data to correct for their fan-beam data acquisition. During the reorganization process, available details of the scanner's raw-data pre-processing, which would be an example of "scanner information" as that term is used herein, can be incorporated by CT imaging simulator 130. The reorganization step can be avoided altogether by, for example, projecting in a slice-by-slice fashion. It is also noted that the outcome of wide-cone helical projection for simulating three dimensional reconstruction is a three-dimensional set. However, at present, most CT scanners are two-dimensional construction type scanners.

Figure 7:
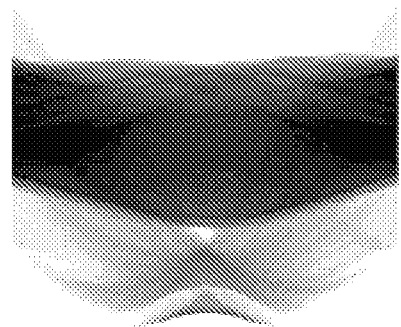
FIG. 7 illustrates a depiction of an attenuation to linear attenuation conversion performed as part of the imaging simulation process according to one non-limiting embodiment.
Figure 7:
Figure 7:
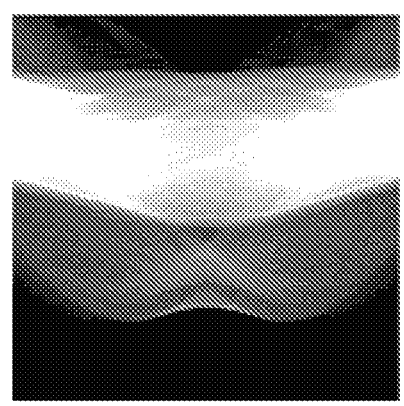

Next, CT imaging simulator 130 can perform an attenuation to linear attenuation conversion in order to convert a raw projection of a single slice into a "sinogram." An example of the effect of this conversion is illustrated in FIG. 7. While the term "sinogram" is used, this step is not intended to be specific to image simulation in two-dimensional reconstruction and can be applied in both two-dimensional and three-dimensional reconstruction schemes. Mathematically, this conversion involves applying the natural logarithm of the magnitude of attenuated projections according to the following equation:

$$-\ln(A_\delta) = -\ln(e^{-\Sigma_{Organs} \mu_{organ} d_{organ}} + \delta)$$

The need for this exponentiation and taking logarithm lies in the additional term in the above formula δ. This term is a randomly generated noise based on an appropriate distribution (e.g., compound Poisson distribution), and depends primarily on the x-ray tube current and certain other attributes of the scanner, such as the detector efficiency. An electronic noise may also be added to this term when high-accuracy image simulation for a specific scanner is intended and proprietary scanner information is available.

Figure 8:
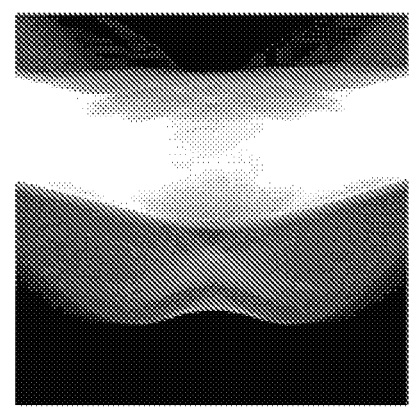
FIG. 8 illustrates a depiction of a simulated slice image generated as part of the imaging simulation process according to one non-limiting embodiment.
Figure 8:
Figure 8:
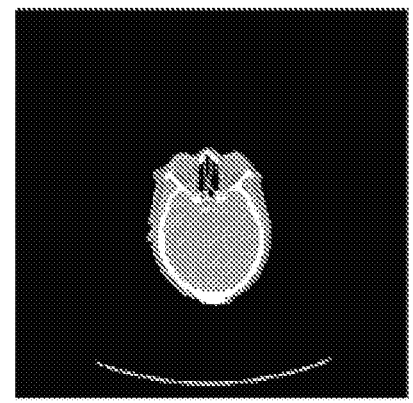

Next, CT imaging simulator 130 can perform reconstruction, which may constitute the final step in image simulation. Once the "sinograms" discussed above, which may be more appropriately referred to as noisy linear-attenuation projections, are compiled, reconstruction can be performed in order to convert the "sinograms" into a simulated slice image. An example of the effect of this conversion is illustrated in FIG. 8. While reconstruction, and image simulation for that matter, are capable of capturing the main effects of photon starvation due to low tube current and insufficient kVp, the accuracy of simulated images can be improved by incorporating the specifics of the reconstruction algorithm employed by the subject CT scanner.

As would be understood by a person skilled in the art, various reconstruction algorithms may be employed, depending on the specifics of the subject CT scanner. For example, for two-dimensional reconstruction, reconstruction algorithms can be, for example, filtered back projection (FBP) or iterative (algebraic) reconstruction. Three-dimensional reconstruction can be based on the Feldkamp-Davis-Kress (FDK) algorithm or Katsevich's exact reconstruction algorithm. Other suitable reconstruction methods include those discussed in United States Patent Application Publication No. 2016/0367212 to Tang, et al. and United States Patent Application Publication No. 2013/0315453 to Cao, each of which is expressly incorporated herein by reference. As mentioned above, the artifacts in the reconstructed CT images depend on the details of the algorithm used for reconstructing the images.

Upon completion of the reconstruction process, the output is a simulated CT image. In the embodiment shown in FIG. 8, the simulated CT image is in the form of a simulated slice image. The image simulation steps can be repeated to generate additional simulated images of different slices of the phantom. The simulated images can be compiled and displayed on a display associated with CT imaging simulator 130 where they can be reviewed by a user. The simulated images can also be sent via wired or wireless communication means to another review device that may be remote from the CT imaging simulator, such as a personal computer, handheld device such as a smartphone, laptop, or PDA, or another device having a display screen capable of displaying the simulated images. In addition, the simulated images can be stored in a database for future use and review.

Various uses are contemplated for CT imaging simulator 130. In one non-limiting embodiment, the CT imaging simulator 130 is used as a prospective tool for improving and optimizing existing CT imaging protocols as well as designing new custom protocols. By way of example, CT imaging simulator 130 can be used to generate simulated images so as to test whether a particular imaging protocol will provide CT images of the subject patient that have sufficient resolution. Based on a review of the simulated images, adjustments to the imaging protocol can be made. These adjustments can include reducing the overall radiation applied as part of the CT scan if, for example, the simulated images have an overabundance of resolution for the task at hand. By way of another example, a radiologist can use CT image simulator 130 to test various custom protocols before having to test such protocols on actual patients.

In another non-limiting embodiment, CT imaging simulator 130 can be used together with existing Monte-Carlo-based organ dose estimation tools, such as those discussed in U.S. Pat. Nos. 8,953,861 and 9,792,680 and United States Patent Application Publication Nos. 2017/0123074 and 2017/0228860, which are expressly incorporated herein by reference, to provide a comprehensive picture of CT imaging that includes both radiation dose and image quality aspects.

In another non-limiting embodiment, CT imaging simulator 130 can be used as a tool for retrospective analysis of CT images to address questions such as whether it would have been possible to reduce the radiation dose without compromising the diagnosis, or how much improvement in image quality would have been achieved if a contrast agent were used.

In yet another non-limiting embodiment, CT imaging simulator 130 can be used as an economical research or training tool, such as in an educational setting to provide simulated images that can be studied and discussed.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

The invention claimed is:

1. A method of generating simulated CT images of a subject patient, comprising:
    receiving patient information about the subject patient, wherein the patient information comprises information about one or more physical properties of the subject patient;
    selecting, from a phantom database, a virtual phantom, wherein the selection is based on a comparison of the patient information with characteristics of the virtual phantom;
    receiving, at a CT imaging simulator, the virtual phantom;
    receiving, at the CT imaging simulator, scanner information about a subject CT scanner, wherein the scanner information comprises information about an image reconstruction technique employed by the subject CT scanner;
    performing, by the CT imaging simulator, an image simulation process, wherein the image simulation process comprises generating a simulated CT image using the virtual phantom and the scanner information; and
    providing the simulated CT image on a display screen in a visually perceptible form.

2. The method of claim 1, further comprising:
    deforming the virtual phantom, wherein deforming the virtual phantom comprises one or more of adjusting the shape of organs in the virtual phantom, adjusting tissue densities in the virtual phantom using the patient information, and incorporating an implant into the virtual phantom.

3. The method of claim 2, wherein deforming the virtual phantom comprises adjusting the tissue densities using the patient information, wherein the patient information comprises bone density information of the subject patient.

4. The method of claim 2, wherein deforming the virtual phantom comprises incorporating the implant into the virtual phantom.

5. The method of claim 1, wherein at least a portion of the scanner information is received from a scanner database in communication with the CT imaging simulator.

6. The method of claim 1, wherein at least a portion of the scanner information is received from a user interface associated with the CT imaging simulator, wherein the at least a portion of the scanner information has been manually entered by a user into the user interface.

7. The method of claim 1, wherein the CT imaging simulator is in communication with the subject CT scanner and at least a portion of the scanner information is received from the subject CT scanner.

8. The method of claim 1, further comprising:
   receiving, at the CT imaging simulator, an identity of the subject CT scanner; and
   querying, by the CT imaging simulator, a scanner database for scanner information about the subject CT scanner, wherein the query is based on the identity of the subject CT scanner.

9. The method of claim 1, wherein selecting the virtual phantom is performed by the CT imaging simulator based on a comparison of the patient information with characteristics of the virtual phantom done by the CT imaging simulator.

10. The method of claim 1, wherein the one or more physical properties of the subject patient include at least one of age, height, body size, sex, weight, and body mass index.

11. The method of claim 1, wherein the image simulation process comprises generating projection images.

12. The method of claim 1, wherein the image simulation process comprises performing an attenuation to linear attenuation conversion according to the following equation:

$$-\ln(A_\delta) = -\ln(e^{-\Sigma_{Organs} \mu_{organ} d_{organ}} + \delta).$$

13. The method of claim 1, wherein the image simulation process comprises performing a reconstruction in order to generate a simulated slice image.

14. A system, comprising:
   a CT imaging simulator, comprising a user interface, a display screen, a processor, and a non-transitory storage medium comprising programming instructions;
   a phantom database in communication with the CT imaging simulator, wherein the phantom database comprises one or more virtual phantoms; and
   a scanner database in communication with the CT imaging simulator, wherein the scanner database comprises information about one or more CT scanners, including a subject CT scanner;
   wherein the programming instructions, if executed, enable the processor to:
      receive patient information about a subject patient, wherein the patient information comprises information about one or more physical properties of the subject patient;
      receive from the phantom database a virtual phantom, wherein the virtual phantom has been selected based on a comparison of the patient information with characteristics of the virtual phantom;
      receive scanner information about the subject CT scanner, wherein the scanner information comprises information about an image reconstruction technique employed by the subject CT scanner;
      perform an image simulation process, wherein the image simulation process comprises generating a simulated CT image using the virtual phantom and the scanner information; and
      provide the simulated CT image on the display screen in a visually perceptible form.

15. The system of claim 14, wherein the programming instructions, if executed, further enable the processor to receive at least a portion of the scanner information from the scanner database.

16. The system of claim 15, wherein the programming instructions, if executed, further enable the processor to query the scanner database for scanner information about the subject scanner, wherein the query is based on an identity of the subject CT scanner.

17. The system of claim 14, wherein the programming instructions, if executed, further enable the processor to deform the virtual phantom, wherein deforming the virtual phantom comprises one or more of adjusting the shape of organs in the virtual phantom, adjusting tissue densities in the virtual phantom using the patient information, and incorporating an implant into the virtual phantom.

18. CT imaging simulator software stored on a non-transitory storage medium to generate a simulated CT image of a subject patient, the CT imaging simulator software comprising programming instructions that, if executed, enable a processor to:
   receive patient information about the subject patient, wherein the patient information comprises information about one or more physical properties of the subject patient;
   receive a virtual phantom, wherein the virtual phantom has been selected based on a comparison of the patient information with characteristics of the virtual phantom;
   receive scanner information about a subject CT scanner, wherein the scanner information comprises information about an image reconstruction technique employed by the subject CT scanner;
   perform an image simulation process, wherein the image simulation process comprises generating a simulated CT image using the virtual phantom and the scanner information; and
   provide the simulated CT image in a visually perceptible form.

19. The CT imaging simulator software of claim 18, wherein the programming instructions, if executed, further enable the processor to receive at least a portion of the scanner information from a scanner database.

20. The CT imaging simulator software of claim 19, wherein the programming instructions, if executed, further enable the processor to query the scanner database for scanner information about the subject CT scanner, wherein the query is based on an identity of the subject CT scanner.

21. The CT imaging simulator software of claim 18, wherein the programming instructions, if executed, further enable the processor to deform the virtual phantom, wherein deforming the virtual phantom comprises one or more of adjusting the shape of organs in the virtual phantom, adjusting tissue densities in the virtual phantom using the patient information, and incorporating an implant into the virtual phantom.

* * * * *

UNITED STATES PATENT AND TRADEMARK OFFICE
CERTIFICATE OF CORRECTION

PATENT NO.         : 11,000,255 B2
APPLICATION NO.    : 16/482845
DATED              : May 11, 2021
INVENTOR(S)        : Mohammad Sedigh Ghamari It is certified that error appears in the above-identified patent and that said Letters Patent is hereby corrected as shown below:

In the Specification
In Column 1, Line 8, delete "a 371" and insert -- a 35 USC § 371 --, therefor.
In Column 5, Line 16, delete "computerized tomography (CT)" and insert -- computed tomography (CT) --, therefor.
In Column 5, Line 26, delete "CT image simulations" and insert -- CT imaging simulations --, therefor.
In Column 11, Line 23, delete "kVP." and insert -- kVp. --, therefor.
In Column 12, Line 37, delete "$\mu_{Organ}$" and insert -- $\mu_{organ}$ --, therefor.
In Column 12, Line 38, delete "$d_{Organ}$" and insert -- $d_{organ}$ --, therefor.
In Column 13, Line 67, delete "CT image" and insert -- CT imaging --, therefor.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*